United States Patent
Greene (10) Patent No.: US 10,258,257 B2
(45) Date of Patent: Apr. 16, 2019

(54) QUANTITATIVE FALLS RISK ASSESSMENT THROUGH INERTIAL SENSORS AND PRESSURE SENSITIVE PLATFORM

(75) Inventor: Barry Greene, Dublin (IE)

(73) Assignee: KINESIS HEALTH TECHNOLOGIES LIMITED, Dublin (IE)

(*) Notice: Subject to any disclaimer, the term of this patent is extended or adjusted under 35 U.S.C. 154(b) by 1236 days.

(21) Appl. No.: 13/554,720

(22) Filed: Jul. 20, 2012

(65) Prior Publication Data
US 2014/0024972 A1    Jan. 23, 2014

(51) Int. Cl.
| | |
|---|---|
| A61B 5/103 | (2006.01) |
| A61B 5/11 | (2006.01) |
| A61B 5/00 | (2006.01) |
| G06F 19/00 | (2018.01) |

(52) U.S. Cl.
CPC .......... *A61B 5/1038* (2013.01); *A61B 5/1117* (2013.01); *A61B 5/7275* (2013.01); *G06F 19/00* (2013.01); *A61B 5/742* (2013.01)

(58) Field of Classification Search
CPC ..................................................... A61B 5/00
USPC .............. 600/300, 587, 590, 595; 482/142
See application file for complete search history.

(56) References Cited

U.S. PATENT DOCUMENTS

| | | | | |
|---|---|---|---|---|
| 5,388,591 | A * | 2/1995 | De Luca | A61B 5/4023 600/592 |
| 6,063,046 | A * | 5/2000 | Allum | A61B 5/1036 600/595 |
| 6,852,086 | B2 * | 2/2005 | Atlas | A61B 5/0205 600/587 |
| 7,361,150 | B2 * | 4/2008 | Berthonnaud | A61B 5/103 33/515 |
| 7,526,071 | B2 * | 4/2009 | Drapeau | A61B 5/0064 378/163 |

(Continued)

FOREIGN PATENT DOCUMENTS

| | | |
|---|---|---|
| WO | 2011002788 | 1/2011 |
| WO | 2011016782 | 2/2011 |
| WO | 2012094486 | 7/2012 |

OTHER PUBLICATIONS

Walsh et al., "Development and Validation of a Clinic Based Balance Assessment Technology", 33rd Annual International Conference of the IEEE EMBS, Aug. 30-Sep. 3, 2011, pp. 1327-1330.
Greene et al., "Quantitative Falls Risk Assessment Using the Timed Up and Go Test", IEEE Transactions on Biomedical Engineering, vol. 57, No. 12, Dec. 2010, pp. 2918-2926.

(Continued)

*Primary Examiner* — May A Abouelela
(74) *Attorney, Agent, or Firm* — Davé Law Group, LLC; Raj S. Davé

(57) ABSTRACT

A system, method, and apparatus is provided for estimating a risk of falls from pressure sensor data and inertial sensor data. A classifier function may be generated to relate the inertial sensor and the pressure sensor data with the falls risk (e.g., falls risk or prospective falls data) of the person who generated the pressure sensor data and inertial sensor data. The classifier function may be used to predict a person's risk of falls based on inputs of pressure sensor data and inertial sensor data. Separate classifier functions may be generated for men and women, or separate classifier functions may be generated for patients who closed their eyes while data was being collected and for patients who opened their eyes while data was being collected.

21 Claims, 6 Drawing Sheets

(56) References Cited

U.S. PATENT DOCUMENTS

| | | | | |
|---|---|---|---|---|
| 8,011,229 | B2* | 9/2011 | Lieberman | A61B 5/1036 73/65.01 |
| 8,092,355 | B2* | 1/2012 | Mortimer | A63B 24/00 482/1 |
| 8,109,890 | B2* | 2/2012 | Kamiar | A61B 5/1038 600/595 |
| 8,405,510 | B2* | 3/2013 | Shieh | A61B 5/4023 340/407.1 |
| 8,529,448 | B2* | 9/2013 | McNair | A61B 5/00 600/300 |
| 8,852,128 | B2* | 10/2014 | Bhattacharya | A61B 5/1036 482/129 |
| 2002/0077567 | A1* | 6/2002 | McLeod | A61B 5/1036 600/587 |
| 2005/0010139 | A1* | 1/2005 | Aminian | A61B 5/1038 600/595 |
| 2005/0182341 | A1* | 8/2005 | Katayama | A61B 5/103 600/587 |
| 2006/0282017 | A1* | 12/2006 | Avni | A61B 5/1036 600/587 |
| 2008/0108913 | A1* | 5/2008 | Lengsfeld | A61B 5/1038 600/595 |
| 2008/0285805 | A1* | 11/2008 | Luinge | G06F 3/011 382/107 |
| 2009/0048540 | A1* | 2/2009 | Otto | A61B 5/1118 600/595 |
| 2009/0062092 | A1* | 3/2009 | Mortimer | A63B 24/00 482/142 |
| 2010/0210975 | A1* | 8/2010 | Anthony, III | A61B 5/0002 600/595 |
| 2011/0172562 | A1* | 7/2011 | Sahasrabudhe | A61B 5/0476 600/587 |
| 2011/0190593 | A1* | 8/2011 | McNair | A61B 5/00 600/300 |
| 2012/0092169 | A1* | 4/2012 | Kaiser | A61B 5/1038 340/573.1 |
| 2012/0232430 | A1* | 9/2012 | Boissy | A61B 5/1118 600/595 |

OTHER PUBLICATIONS

Greene et al., "Evaluation of Falls Risk in Community-Dwelling Older Adults Using Body-Worn Sensors", Regenerative and Technological Section/Original Paper, Gerontology 2012; 59;472-480, along with supplementary table.

Greene et al., "Quantitative falls risk estimation through multi-sensor assessment of standing balance", Physiological Measurement, Physiol. Meas. 33 (2012) pp. 2049-2063.

Extended European Search Report in corresponding EP Patent Application: 13177482.0. dated Dec. 12, 2014. (10 pages).

Foroughi, H. et al. "Robust Fall Detection Using Human Shape and Multi-class Support Vector Machine" Sixth Indian Conference on Computer Vision, Graphics & Image Processing. pp. 413-420. ISBN: 978-0-7695-3476-3. XP031409478. Date: Dec. 16, 2008.

Greene, Barry R. et al., Assessment of Cognitive Decline Through Quantitative Analysis of the Timed Up and Go Test, IEEE Transactions on Biomedical Engineering, vol. 59, No. 4, Apr. 2012, pp. 988-995.

Greene, Barry R. et al., Body-worn sensor based surrogates of minimum ground clearance in elderly fallers and controls, 33rd Annual International Conference of the IEEE EMBS, Boston, Massachusetts USA, Aug. 30-Sep. 3, 2011.

Greene, Barry R. et al., Adaptive estimation of temporal gait parameters using body-worn gyroscopes, 32nd Annual International Conference of the IEEE EMBS, Buenos Aires, Argentina, Aug. 31-Sep. 4, 2010.

Greene, Barry R. et al., Falls risk assessment through quantitative analysis of TUG, Mar. 21, 2010.

Donovan, Karol J. et al., SHIMMER: A new tool for temporal Gait analysis, 31st Annual International Conference of the IEEE EMBS, Minneapolis, Minnesota, USA, Sep. 2-6, 2009.

Doheny, Emer P., et al., A single gyroscope method for spatial gait analysis, 32nd Annual International Conference of the IEEE EMBS, Buenos Aires, Argentina, Aug. 31-Sep. 4, 2010.

McGrath, Denise et al., Estimation of minimum ground clearance (MGC) using body-work inertial sensors, Journal of Biomechanics 44 (2011), pp. 1083-1088.

Greene, Barry R. et al., An adaptive gyroscope-based algorithm for temporal gait analysis, Med Biol Eng Computn Nov. 2010, vol. 48, pp. 1251-1260.

* cited by examiner

| Pressure sensor features | Inertial sensor features |
|---|---|
| Mean COP dist | Mean RMS Acc |
| RMS COP dist | RMS Acc (ML) |
| Sway length | RMS Acc (V) |
| Mean sway velocity | RMS Acc (AP) |
| | Mean RMS ang. vel. |
| Demographic | RMS ang. vel. (ML) |
| Age | RMS ang. vel. (V) |
| Gender | RMS ang. vel. (AP) |
| Height | Median frequency Acc (Fmed) |
| Weight | Spectral edge frequency Acc (SEF) |
| | Spectral entropy Acc (H) |

QUANTITATIVE FALLS RISK ASSESSMENT THROUGH INERTIAL SENSORS AND PRESSURE SENSITIVE PLATFORM

This application claims priority under 35 U.S.C. § 120 and § 119 to U.S. patent application Ser. No. 13/198,343, filed Aug. 4, 2011, which claims priority to U.S. Provisional Patent Application Ser. No. 61/470,453, filed Mar. 31, 2011, the entire contents of which are incorporated herein by reference.

FIELD OF THE INVENTION

The invention relates to sensing devices and methods that may be used to estimate a risk of falling.

BACKGROUND OF THE INVENTION

Falls have been considered a "geriatric giant" and are associated with negative health outcomes such as serious injury, hospitalization, restricted mobility, and institutionalization. Falls have a negative effect on quality of life, lead to increased hospitalization, and are costly. The cost of falls each year among the elderly in the U.S. alone has been estimated to be about $20 billion. Falls in older adults are common and their incidence increases with age.

Older people who are prone to falls are more likely to demonstrate abnormalities in postural stability and balance control. Such abnormalities have been measured in clinical settings that have required the use of specialized equipment, such as force plates or optical motion capture systems that measure a patient's center of pressure (COP). Such techniques may be expensive because of the need for clinical visits, specialized equipment, and trained personnel.

SUMMARY OF THE INVENTION

One aspect of the invention relates to a system and method for measuring balance and postural stability based on pressure sensor data and inertial sensor data collected from a person during a standing test. The pressure sensor data may be collected from a portable pressure sensor matrix that has a plurality of pressure sensors that measure a person's pressure distribution as the person stands on the portable pressure sensor matrix. The inertial sensor data may be collected from an inertial sensor attached to the person. The collected data may be used to calculate one or more features, such as statistical properties of center of pressure (COP) calculated from the pressure sensor data or statistical properties of accelerations or angular velocities calculated from the inertial sensor data. Values of the features may be used to train a classifier model. That is, the classifier model may be trained to recognize features patterns associated with self-reported risk of falling. The training may be performed with values collected from a plurality of people. Once trained, the classifier model may be used to estimate an unseen person's risk of falling based on feature values calculated from new sensor data collected from the person. A single classifier model may be created for both men and women, or separate classifier models may be created, with one to predict falls risk in men and one to predict falls risk in women. A single classifier model may be created for bath sensor data collected while a person closed his or her eyes and sensor data collected while the person opened his or her eyes, or separate classifier models may be created, with one for the eyes closed condition and one for the eyes open condition. The timely determination of falls risk would facilitate appropriate intervention, such as a tailored balance and strengthening program, that could reduce the risk of future falls.

In an embodiment, the pressure sensor matrix may include a high density pressure sensitive floor mat having a plurality of sensors that collect pressure sensor data generated from the presence of a person on the mat, while the inertial (kinematic) sensor may include an accelerometer, gyroscope, or magnetometer. Pressure sensor data may be binary, such as the presence or absence of a threshold pressure, or may have more granular values corresponding to the amount of pressure. The pressure sensor data may be collected at a plurality of times. The data corresponding to one of the plurality of times may make up a series of time samples (or snapshots) of pressure sensor data. For example, a center of pressure (COP) may be calculated for each snapshot to produce a COP time series that corresponds to measurements taken over the duration of a balance assessment test. Standard time and frequency domain measures for quantifying the center of pressure may be used to quantify the data obtained during the assessment.

The measurement system may be portable, and the pressure sensor matrix and inertial sensor may be used in a clinical setting or in the home. For example, a measurement of postural stability may be done in a home environment with a pressure sensor matrix, without requiring supervision from specially trained personnel. This unsupervised assessment may reduce the cost of falls assessment and facilitate the gathering of data in a longitudinal (e.g., daily) monitoring of falls risk, such as in a tele-healthcare or tele-monitoring context.

These and other aspects, features, and characteristics of the present invention, as well as the methods of operation and functions of the related elements of structure and the combination of parts and economies of manufacture, will become more apparent upon consideration of the following description and the appended claims with reference to the accompanying drawings, all of which form a part of this specification, wherein like reference numerals designate corresponding parts in the various figures. It is to be expressly understood, however, that the drawings are for the purpose of illustration and description only and are not intended as a definition of the limits of the invention. As used in the specification and in the claims, the singular form of "a", "an", and "the" include plural referents unless the context clearly dictates otherwise.

DETAILED DESCRIPTION

Figure 1A:
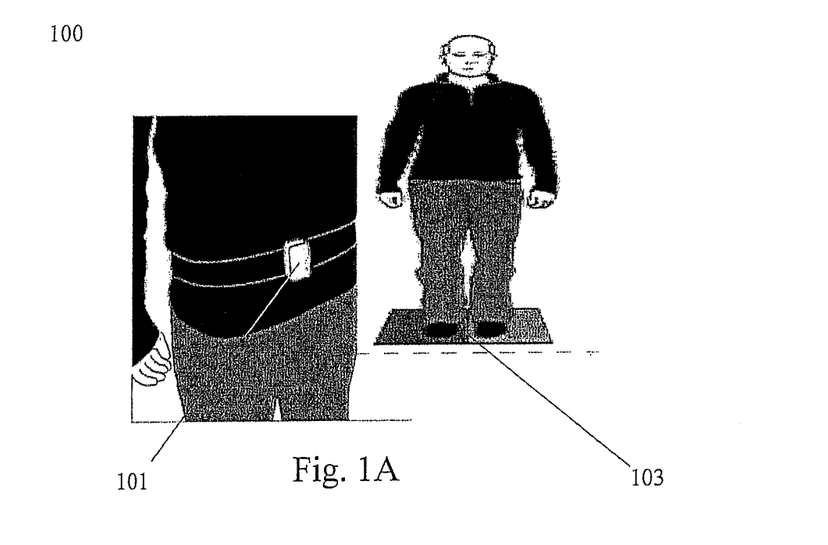
FIG. 1A illustrates an example setup for collecting pressure sensor data and inertial sensor data from a balance assessment trial participant.

One aspect of this invention is directed toward assessing balance and estimating an individual's risk of falling using pressure and inertial sensor data collected from the individual. FIG. 1 illustrates a standing balance assessment environment 100 in which an inertial (kinematic) sensor 101 and a pressure sensor matrix 103 collect kinematic and pressure data, respectively, from a standing balance assessment trial participant. An algorithm may process the pressure sensor data and inertial sensor data to calculate balance-related features, which may be used by falls risk estimation models to predict a risk of future falls. Such models may include classifier models that can be trained with values of the balance-related features and labeled with known corresponding falls history or prospective follow-up data. Such class labels may provide the basis for supervised training of the classifier models. The data gathering may be a part of a clinical balance assessment, or may be used as part of a daily or longitudinal monitoring program done in a person's home. The data gathering may be done with or without medical supervision.

Collecting the pressure sensor data, such as center of pressure (COP) data, is discussed in more detail in U.S. patent application Ser. No. 13/198,343, entitled "Algorithm for Quantitative Standing Balance Assessment," the entire content of which is incorporated by reference herein. As discussed in U.S. patent application Ser. No. 13/198,343, the pressure sensors may be configured as a pressure sensor matrix capable of measuring pressure as a function of a plurality of coordinates (e.g., X coordinate and Y coordinate) that correspond to locations on the matrix. For example, the pressure sensor matrix may be a high-density pressure mat, such as the floor mat pressure sensor provided by Tactex™, which generates pressure sensor data using KINOTEX® technology. The pressure matrix may be rigid, or may be flexible to assist in portability. The pressure sensor matrix may present an area large enough to measure how a person distributes his or her pressure over time on the matrix. Measuring the pressure distribution over time may yield, for example, a trajectory of the person's center of pressure when he or she is standing. The pressure sensors in the matrix may be configured to detect the presence of a threshold pressure, a pressure value, or a change in pressure value, or some combination thereof. For example, the pressure sensors may produce only a binary value that indicates whether the applied pressure is greater than a threshold pressure. In another example, the pressure sensor may produce a pressure value in a range from 0.1 kPa to 200 kPa, or some other range. The range of operation for the pressure sensors may be any range configured to support detecting movement, changes in posture, or changes in balance of a human or other animal. In one example, changes may be recorded when a certain number of sensors (e.g., 200) are deemed to have changed in output. In one example, changes may be recorded periodically, such as at a sampling rate of 10 Hz.

The inertial sensors may include an accelerometer, gyroscope, magnetometer, global positioning system (GPS) transceiver, RFID tag, or any other sensor configured to detect movement. For example, inertial sensors may be sensors based on the SHIMMER™ sensor platform, which includes a 3-axis accelerometer, a battery, and electronic storage. In one example, a inertial sensor may be attached to the lower back of a trial participant, such as to his or her L3 lumbar. The accelerometer may be oriented so that the Y gyroscope sensor axis captures movement about the anatomical medio-lateral axis.

The pressure sensor matrix and inertial sensor may be configured to communicate sensor data over a wired interface or over a wireless interface, such as WLAN or Bluetooth. The sensor data may be communicated to a computing platform such as a desktop, laptop, mobile phone, or other mobile device. For example, the inertial sensor may be sampled through a wireless connection at a rate of 102.4 Hz.

Referring back to FIG. 1A, the standing balance assessment trial participant may be instructed to remain in a comfortable stance during each balance test and may also be instructed to gaze fixed forward. Participants may hold their arms by their side, or may extend their arms outward from their bodies. The participant may stand with both eyes open or both eyes closed. In some instances, stances may vary based on whether the participant has eyes open or eyes closed. A participant with eyes open may be instructed to stand in a semi-tandem stance (e.g., the first metatarsal head of one foot placed beside the heel of the other foot), while a participant with eyes closed may be instructed to stand in a narrow stance (e.g., heels and first metatarsal heads of left and right feet touching).

Figure 1B:
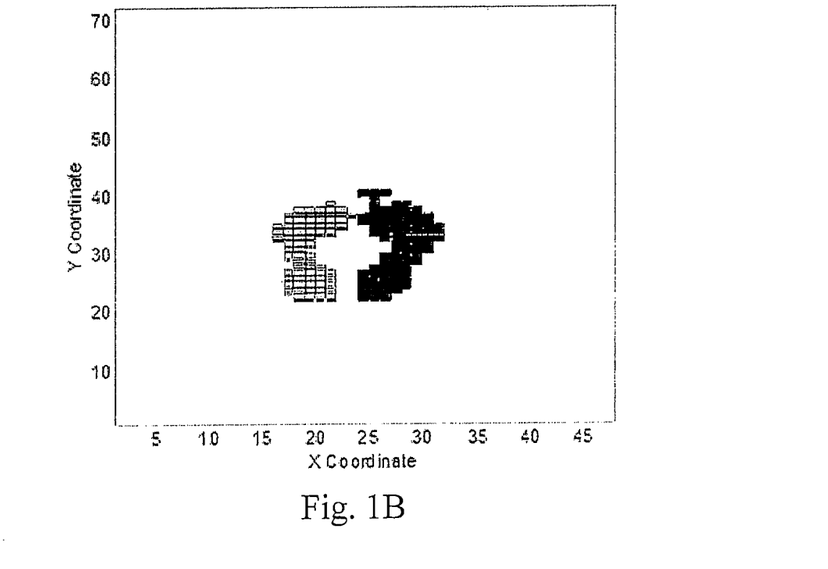
FIG. 1B illustrates an example graphical view of data collected using a pressure sensor matrix.

Each test may last from a few seconds to a few minutes. In one example, each test may last approximately sixty seconds, and pressure sensor data may be collected during the middle thirty seconds. Multiple tests, such as repetitions of the same balance test, may be conducted with the same test participant. In one example, there may be between one to two minutes of rest between tests. Each time a certain number (e.g., 200) of sensors in the sensor matrix are deemed to have changed, the pressure sensor data from those or from all sensors may be captured. An example snapshot of the captured pressure sensor data is shown in FIG. 1B. The pressure sensor matrix may be calibrated to exclude data from pressure sensors that measure less than a threshold level of pressure. The pressure sensors that measure a pressure above the threshold may be considered active sensors, located in an area of the pressure sensor matrix on which the trial participant is standing.

Center of pressure data may be calculated from the pressure sensor data. In an embodiment, a center of pressure may be calculated using a center of all active tactels (CAAT) technique, in which the location of the center of pressure is calculated as the absolute center of all active pressure sensors. In this and other embodiments, the center of pressure data may vary based on time. In an embodiment, the center of pressure may be calculated using a centroid of heel and toe points (CHAT) technique, in which locations of four points, corresponding to two heel points and two toe points, are first calculated from the active pressure sensors. The four points are used to estimate the center of pressure. In an embodiment, the center of pressure may be calculated based on a center of mass (COM) technique, in which a pressure sensor's value is treated as an amount of a user's mass distributed at the pressure sensor. The center of pressure is determined based on the locations of the active pressure sensors as well as based on the values measured by the pressure sensors at their respective locations.

In some instances, video data of a trial participant may be acquired during each test. The video data may be used to later assess the validity of other data acquired from the test.

Figure 2:
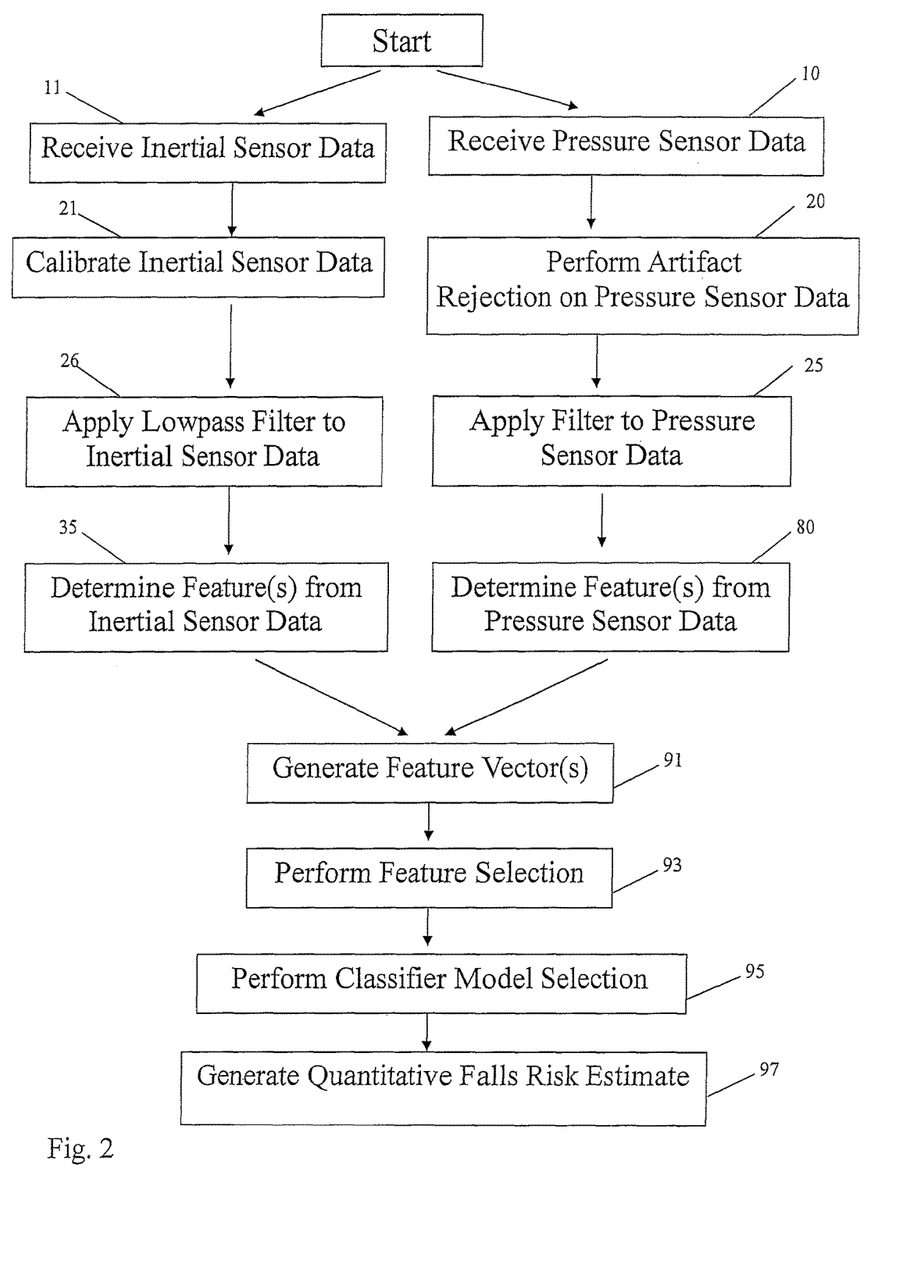
FIG. 2 illustrates example operations that may be performed to generate a quantitative falls risk estimate based on pressure and inertial sensor data from a participant performing a standing balance trial.

To gauge a participant's postural stability and balance, the pressure and inertial sensor data may be collected to determine properties of, for example, the participant's movement and center of pressure, using techniques such as those described above. FIG. 2 illustrates an example overview of operations in such a falls risk assessment environment. At operation 10, pressure sensor data may be collected for an interval of 30 seconds. At operation 11, inertial sensor data may be collected for an interval of 30 seconds. The intervals may be shorter, such as for a few seconds, or longer, such as for a few minutes. The data collection may take place at the beginning, middle, end, or some other interval of a balance assessment trial. At operation 20, artifact rejection may be performed to remove spurious pressure sensor data. For example, a spike in measured pressure values may be rejected, or a series of pressure values exhibiting large fluctuations may be rejected. The pressure sensor data values may also be compared with video data to identify times during which, for example, a test participant was not performing the standing balance task correctly. Pressure sensor data during those times may be excluded. At operation 21, calibration may be performed on the inertial sensor data. For example, accelerometer data from an inertial sensor may be corrected for the effects of gravity, and an initial and terminal five seconds of accelerometer data may be ignored.

At operations 25 and 26, the pressure sensor data and inertial sensor data may be filtered. In one example, a high pass filter may be applied to both sets of data to remove noise. In another example, if a high pass filter is not applied, a bandpass filter of 0.1-5 Hz may be applied to the accelerometer data.

At operation 80, features that relate to the pressure sensor data may be derived. One or more of the features may be derived from, for example, pressure measurements made by pressure sensor matrix 103 or from center of pressure (COP) data calculated from such measurements. The one or more features may include a mean distance, or MDIST, between each COP point for a plurality of snapshots and a mean of the COP points. The one or more features may include a root mean squared of the distances, or RDIST, between each COP point for the plurality of snapshots and the mean COP point. The one or more features may include a sway length, or TOTEX, which measures a total COP path length as the COP varies across the plurality of snapshots. Each snapshot may include a matrix of samples taken from a sensor matrix at a given time. The one or more features may include a mean sway velocity, or MVELO, which measures the mean velocity of the COP over the recording period. The one or more features may include a mean sway area, mean sway frequency, mean sway frequency in a medio-lateral (ML) direction, mean sway frequency in an anterior-posterior (AP) direction, a 95% confidence sway circle area, and a 95% confidence sway ellipse area. Mean sway frequency along the AP direction may be calculated as the rotation frequency of the COP if it travelled around a circle with a radius of the mean COP distance.

As described in application Ser. No. 13/198,343, the mean COP distance, or MDIST, may be calculated as $$MDIST = \frac{1}{N}\sum RD[n] = \frac{1}{N}\sum \sqrt{(AP[n]^2 + ML[n]^2)}$$

where AP and ML represent anterior-posterior and mediolateral coordinates, respectively, of a COP value relative to a mean COP coordinate. More specifically, $AP[n]=APo[n]-\overline{AP}$ and $ML[n]=MLo[n]-\overline{ML}$. $\overline{AP}$ represents the mean anterior-posterior COP coordinate over the recording period, and is calculated as $$\overline{AP} = \frac{1}{N}\sum APo[n].$$

APo[n] represents the anterior-posterior coordinate of the COP at snapshot n of the recording period. $\overline{ML}$ represents the mean mediolateral COP coordinate over the recording period, and is calculated as $$\overline{ML} = \frac{1}{N}\sum MLo[n].$$

MLo[n] represents the mediolateral coordinate of the COP at snapshot n of the recording period. The features described herein may be calculated relative to the mean COP so as to provide standardized center of pressure (COP) time series coordinates.

The root mean squared of the distances, or RDIST, may be calculated as $$\overline{RDIST} = \sqrt{\frac{1}{N}\sum RD[n]^2}.$$

The sway length, or TOTEX, may be calculated as $$TOTEX = \sum_{n=1}^{N-1} \sqrt{\text{Diff\_AP}(n)^2 + \text{Diff\_ML}(n)^2},$$

where Diff_AP(n) represents the change in the COP coordinates along the anterior-posterior axis during the recording period, and may be calculated as Diff_AP(n)=AP(n+1)−AP(n). Diff_ML(n) represents the change in the COP coordinates along the mediolateral axis during the recording period, and may be recorded as Diff_ML(n)=ML(n+1)−ML(n).

The mean sway velocity, or MVELO, may be calculated as

MVELO=TOTEX/$T$, where $T$ is the recording period.

Calculation of a center of pressure (COP) is described in more detail in U.S. patent application Ser. No. 13/198,343. As described in that application, a COP for an instance in time may be calculated as the average position of all active sensors at that instance, which may include the position of all sensors in the matrix that experienced a pressure above a baseline threshold, or may be calculated based on an average of regional pressure centroids. The regional pressure centroids may include a centroid for each of the toe region and heel region for both the left and right feet. The COP may then be calculated as the average position of the four regional centroids. The COP's calculated from the two techniques may yield different coordinates, or may yield the same coordinates.

Referring back to FIG. 2, features based on the inertial sensor data may be determined at operation 35. One or more of the features may be derived from, for example, acceleration or angular velocity measurements made by a gyroscope (e.g., inertial sensor 101). For example, one feature may include a mean RMS of the acceleration data. One or more features may include a RMS of the acceleration data measured along the medio-lateral (ML) axis, vertical axis, or anterior-posterior (AP) axis. One feature may include a mean RMS of the angular velocity data. One or more features may include a RMS of the angular velocity data measured along the ML, V, or AP axis. One feature, such as the spectral edge frequency (SEF), may measure the frequency of sway (e.g., measure the frequency domain variability of the angular velocity or acceleration signals obtained by an inertial sensor). SEF may be calculated as the frequency below which 95% of the power spectrum of the signal is contained. One feature may calculate the median frequency of the acceleration data ($F_{med}$). $F_{med}$ may be calculated as the frequency below which 50% of the power spectrum is contained. One feature may calculate spectral entropy of the acceleration data (H), which may indicate signal complexity of the sensor data.

Figure 3:
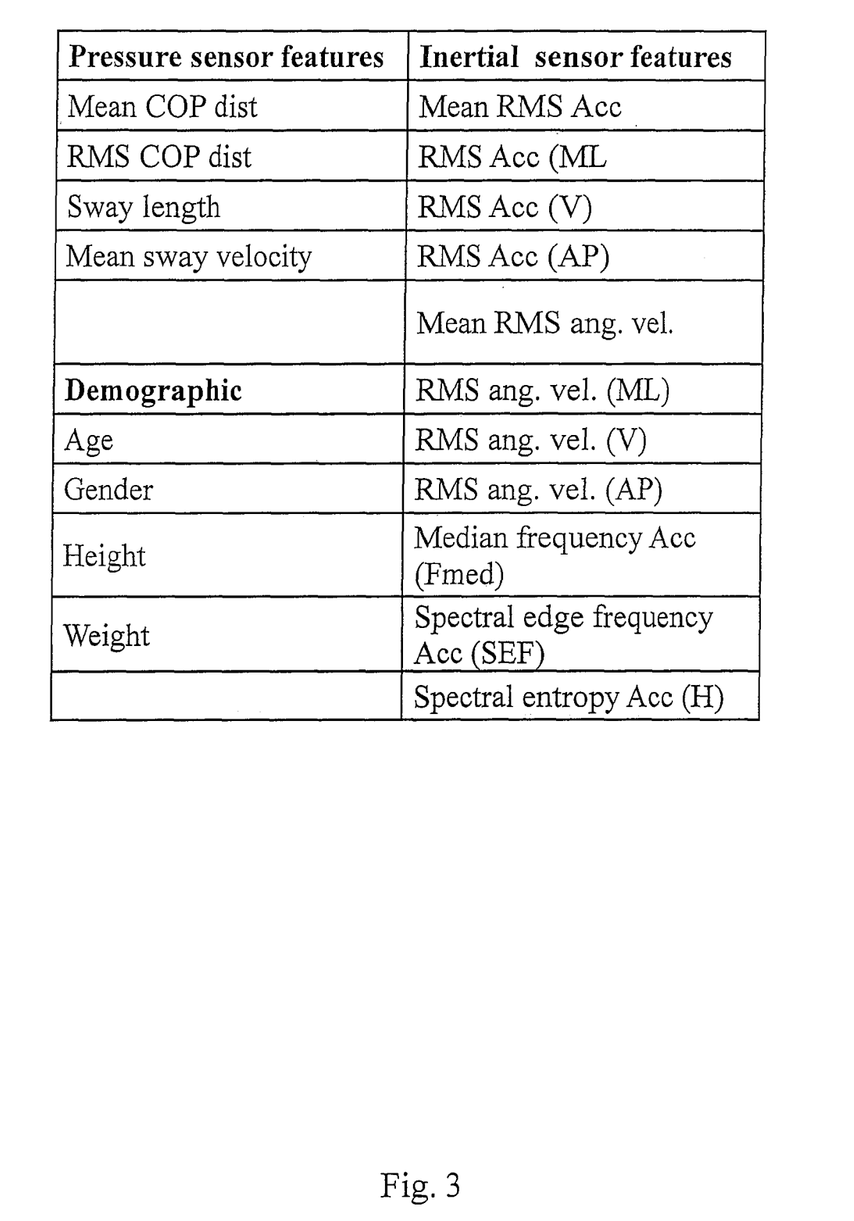
FIG. 3 illustrates example features that may be used in a falls risk estimation model.

Other features for the falls risk estimation model may include demographic information, such as a patient's age, gender, height, or weight. The binary coded gender variable may be used if the falls risk estimation model was generated from data collected from both male and female balance assessment trial participants. FIG. 3 summarizes the example features discussed above.

In some instances, if data had been collected for both a condition in which a participants' eyes remained open and a condition in which the participants' eyes remained closed, a Romberg ratio may be calculated for each of the features discussed above. This ratio may be calculated as the ratio of a feature's value in an eyes closed condition versus the feature's value in an eyes open condition. The Romberg ratio may itself be used as a feature in a falls risk model.

At operation 91, one or more feature vectors may be generated. A feature vector may include one or more features determined at operations 35 and 80. The various feature vectors may divide the features along broad categories, such as features based on inertial sensor data versus features based on pressure sensor data, or such as features based on data collected from male participants versus features based on data collected from female participants. Example vectors are discussed below:

A vector having features based on inertial sensor data and pressure sensor data collected from all balance assessment trials.

A vector having features based on only the inertial sensor data and pressure sensor data collected from male participants.

A vector having features based on only the inertial sensor data and pressure sensor data collected from female participants.

A vector having features based on only pressure sensor data collected from all balance assessment trials.

A vector having features based on only inertial sensor data collected from all balance assessment trials.

A vector having features based on pressure sensor data collected from only trials in which participants kept their eyes open.

A vector having features based on pressure sensor data collected from only trials in which participants kept their eyes closed.

A vector having features based on inertial sensor data collected from only trials in which participants kept their eyes open.

A vector having features based on inertial sensor data collected from only trials in which participants kept their eyes closed.

The falls risk estimation model that is used to estimate future risk of falls may be based on any of the above vectors of features, any other vector of features, or any combination of the vectors of features. At operation 93, an optimal set of features may be determined. For example, sequential forward feature selection may be performed along with a grid search to obtain, for example, optimal support vector machine classifier parameters, such as C or σ. The feature selection may determine an optimal set of features to be used by the falls risk estimation model.

At operation 95, a falls risk estimation model may be selected for performing falls risk estimation. In one embodiment, the selected model may be a classifier model, such as a support vector machine (SVM) model. The SVM may be trained to relate feature values derived from a participant with the participant's self-reported falls history or risk of falling. A SVM maps training vectors ($x_i$) into a higher dimensional space by using a kernel function. The kernel function may include, for example, a radial basis function (RBF), which is defined as:

$K(x_n, x_m) = e^{\sigma ||x_n - x_m||^2}$, where σ>0. The SVM classifier function may find a linear separating hyperplane with the maximal margin in a higher dimensional space. The sequential forward feature selection may determine which features will be included in the SVM model, and may determine optimal SVM parameters, such as the parameter σ of the radial basis function and the box-constraint parameter C. The box-constraint parameter represents a penalty parameter for errors in the SVM model. To determine how performance of the various classifier models, each having a different set of features and SVM parameters, compare against each other, cross validation or a t-test may be performed. For example, a five-fold cross validation may be performed to determine an unbiased estimate of the performance of the various classifier functions. A t-test may be used to determine if the output of one of the classifier models is significantly more accurate than the output of another one of the classifier models.

At operation 97, a quantitative falls risk estimate may be generated by a classifier model. The performance of the classifier may be determined by comparing the falls risk estimate that a model generated for a participant against the participant's self-reported falls risk. In one example, each participant may be classified as a faller or non-faller before his or her balance assessment trial. The classification may be based on risk factor for falls or based on timing of falls.

In classifying a participant based on risk factor for falls, those participants who have not experienced a fall in the previous five years may be classified as a non-faller. Those participants who experienced two or more falls in the previous five years, or who experienced one fall with an accompanying symptom of concern (e.g., fall was unexplained, fall was accompanied by syncope, presyncope or loss of consciousness, pre-fall symptoms of dizziness or light-headedness, fall was accompanied by injuries resulting in fracturing or major injury, participant had chronic pain, participant had fear of falling, participant had physical disability, concern about the fall, or depression following the fall) may be classified as a faller. A participant who had an accidental fall without such symptoms may be classified as a non-faller.

In classifying a participant based on timing of falls, a participant may further be classified into the following categories: not at risk, at risk, Faller 12-months, Faller 6-months, and Recurrent Faller. A participant who has had no falls in the last five years and no problems with balance or walking may be classified into the not at risk category. If the participant had no falls but has problems with balance and walking, the participant may be classified as being at risk. If the participant had one fall in the previous twelve months, the participant may be classified as being in the Faller 12-month category. If the participant had a fall in the previous six months, the participant may be classified as being in the Faller 6-month category. If the participant had two or more falls in the previous 12 months, the participant may be classified as being in the Recurrent Faller category.

Data collected from the participant may be used by the falls risk estimation model to determine the participant's falls risk category. The estimated category may be compared against how the participant was classified from his or her self-reported falls history. Metrics for evaluating the performance of the falls risk estimation model include accuracy (ACC), sensitivity (SENS), specificity (SPEC), positive predictive value (PPV), and negative predictive value (NPV). The ACC value may be calculated as the percentage of participants who were correctly classified as a faller or non-faller when compared against their self-reported falls history. The SENS value may be calculated as the percentage of participants, out of those who were self-reported as fallers, who were correctly classified as fallers. The SPEC value may be calculated as the percentage of participants, out of those who were self-reported as non-fallers, who were correctly classified as non-fallers. The PPV value may be calculated as the percentage of participants, out of those estimated by the model as a faller, who were actually self-reported as fallers. The NPV value may be calculated as the percentage of participants, out of those classified by the model as a non-faller, who were actually self-reported as a non-faller.

One example classifier model and falls risk estimation was obtained from a sample of 120 participants. The sample included 57 male participants and 63 female participants, with an average age of 73.7 years and a standard deviation of 5.8 years. Self-reported falls histories were collected from the participants and used to label each participant as a faller or as a non-faller. Example demographic characteristics of the two categories of participants are shown in Table 1.

TABLE 1

|  | Faller Mean ± Std | Non-faller Mean ± Std |
|---|---|---|
| Age (yrs) | 74.00 ± 5.81 | 73.27 ± 5.77 |
| Height (cm) | 165.65 ± 9.45 | 167.20 ± 9.05 |
| Weight (kg) | 77.20 ± 15.23 | 76.03 ± 13.78 |

In the example balance assessment trials, each participant was asked to complete six standing balance trials. Three of the trials were performed by the participant with his or her eyes open, while three of the trials were performed by the participant with his or her eyes closed. Pressure sensor data and inertial sensor data were collected from the participants during each of the trials. Example values of various calculated features are shown in Table 2. The values are divided among participants who were self-reported as fallers and participants who were self-reported as non-fallers. The values are also divided among trials in which a participant's eyes were open versus trials in which the participant's eyes were closed. The Romberg ratio R, which calculates the ratio of feature values of an eyes open trial to feature values of a eyes closed trial, are also listed below.

TABLE 2

| Variable | Faller EO | Non-faller EO | Faller EC | Non-faller EC |
|---|---|---|---|---|
| Pressure Sensor | | | | |
| Mean COP dist (CAAT) | 41.52 ± 29.24 | 41.10 ± 28.88 | 34.42 ± 28.91 | 37.70 ± 24.17 |
| RMS COP dist (CAAT) | 50.31 ± 32.58 | 50.12 ± 31.49 | 41.70 ± 31.40 | 44.60 ± 26.80 |
| Sway length (CAAT) | 878.14 ± 1028.51 | 858.49 ± 1165.96 | 945.70 ± 1236.88 | 1261.44 ± 1573.11 |
| Mean sway velocity (CAAT) | 43.91 ± 51.43 | 42.92 ± 58.30 | 47.28 ± 61.84 | 63.07 ± 78.66 |
| Mean sway area (CAAT) | 1747.33 ± 3281.59 | 1429.97 ± 2246.93 | 1839.82.29 ± 3852.98 | 2761.10 ± 4482.12 |
| Mean sway frequency (CAAT) | 0.17 ± 0.13 | 0.20 ± 0.18 | 0.21 ± 0.16 | 0.24 ± 0.19 |
| Mean sway frequency (ML) (CAAT) | 0.22 ± 0.16 | 0.24 ± 0.20 | 0.23 ± 0.20 | 0.27 ± 0.26 |
| Mean sway frequency (AP) (CAAT) | 0.20 ± 0.14 | 0.23 ± 0.24 | 0.25 ± 0.17 | 0.28 ± 0.19 |
| 95% CI circle area (CAAT) | 40112.21 ± 40888.38 | 42176.48 ± 39260.88 | 28162.28 ± 31446.82 | 28884.14 ± 25384.67 |
| 95% CI ellipse area (CAAT) | 13576.90 ± 17770.59 | 13335.04 ± 15199.56 | 10832.86 ± 15021.11 | 12388.23 ± 12776.47 |
| Mean COP dist (COM) | 14.29 ± 5.29 | 13.92 ± 4.27 | 13.84 ± 4.24 | 13.05 ± 4.68 |
| RMS COP dist (COM) | 16.35 ± 6.01 | 16.01 ± 5.05 | 15.59 ± 4.83 | 14.78 ± 5.34 |
| Mean sway length (COM) * | 632.55 ± 341.47 | 786.98 ± 485.72 | 577.54 ± 386.90 | 691.56 ± 454.09 |

TABLE 2-continued

| | | | | |
|---|---|---|---|---|
| Mean sway velocity (COM) * | 31.63 ± 17.07 | 39.35 ± 24.29 | 28.88 ± 19.34 | 34.58 ± 22.70 |
| 95% CI circle area (COM) | 2758.29 ± 1980.42 | 2629.44 ± 1541.71 | 2391.85 ± 1520.96 | 2331.07 ± 2343.49 |
| 95% CI ellipse area (COM) | 2017.20 ± 1454.77 | 1850.26 ± 1072.25 | 1864.44 ± 1032.57 | 1789.55 ± 1386.96 |
| Mean sway area (COM) | 56278.75 ± 42580.58 | 66462.38 ± 47167.22 | 51731.09 ± 41634.13 | 57336.21 ± 47241.95 |
| Mean sway frequency (COM) | 0.35 ± 0.17 | 0.45 ± 0.28 | 0.33 ± 0.19 | 0.43 ± 0.26 |
| Mean ML sway frequency (COM) * | 0.38 ± 0.19 | 0.49 ± 0.32 | 0.36 ± 0.20 | 0.49 ± 0.34 |
| Mean AP sway frequency (COM) ^ | 0.42 ± 0.19 | 0.55 ± 0.32 | 0.41 ± 0.25 | 0.51 ± 0.31 |
| Inertial sensor | | | | |
| Mean RMS Acc | 1.00 ± 0.00 | 1.00 ± 0.00 | 1.00 ± 0.00 | 1.00 ± 0.00 |
| RMS Acc (ML) | 0.06 ± 0.03 | 0.04 ± 0.01 | 0.05 ± 0.02 | 0.04 ± 0.01 |
| RMS Acc (V) | 0.03 ± 0.01 | 0.02 ± 0.00 | 0.02 ± 0.01 | 0.02 ± 0.01 |
| RMS Acc (AP) | 0.02 ± 0.01 | 0.02 ± 0.01 | 0.01 ± 0.01 | 0.01 ± 0.00 |
| Mean RMS ang. vel. | 0.02 ± 0.01 | 0.02 ± 0.01 | 0.02 ± 0.01 | 0.02 ± 0.01 |
| RMS ang. vel. (ML) | 2.87 ± 2.01 | 1.95 ± 0.73 | 1.80 ± 1.19 | 1.39 ± 0.53 |
| RMS ang. vel. (V) | 1.49 ± 1.03 | 1.06 ± 0.44 | 0.85 ± 0.57 | 0.62 ± 0.30 |
| RMS ang. vel. (AP) | 1.15 ± 0.67 | 0.85 ± 0.31 | 0.87 ± 0.40 | 0.75 ± 0.28 |
| Median frequency Acc (Fmed) | 0.72 ± 0.46 | 0.49 ± 0.16 | 0.51 ± 0.28 | 0.41 ± 0.16 |
| Spectral edge frequency Acc (SEF) | 1.42 ± 0.36 | 1.42 ± 0.31 | 0.99 ± 0.34 | 0.99 ± 0.21 |
| Spectral entropy Acc (H) | 3.51 ± 0.43 | 3.58 ± 0.37 | 2.88 ± 0.42 | 2.96 ± 0.41 |

| Variable | Faller | Non-faller |
|---|---|---|
| | R | |
| Pressure Sensor | | |
| Mean COP dist (CAAT) | 3.91 ± 6.55 | 4.61 ± 14.14 |
| RMS COP dist (CAAT) | 3.71 ± 6.90 | 3.63 ± 9.75 |
| Sway length (CAAT) | 5.42 ± 11.21 | 3.26 ± 8.26 |
| Mean sway velocity (CAAT) | 5.42 ± 11.21 | 3.26 ± 8.26 |
| Mean sway area (CAAT) | 37.63 ± 127.19 | 153.85 ± 917.01 |
| Mean sway frequency (CAAT) | 1.99 ± 4.24 | 1.26 ± 1.69 |
| Mean sway frequency (ML) (CAAT) | 4.34 ± 14.95 | 1.78 ± 3.64 |
| Mean sway frequency (AP) (CAAT) | 1.29 ± 1.31 | 1.17 ± 1.33 |
| 95% CI circle area (CAAT) | 86.82 ± 299.46 | 191.24 ± 931.31 |
| 95% CI ellipse area (CAAT) | 33.44 ± 103.85 | 182.28 ± 1108.24 |
| Mean COP dist (COM) | 1.10 ± 0.45 | 1.13 ± 0.38 |
| RMS COP dist (COM) | 1.12 ± 0.47 | 1.15 ± 0.38 |
| Mean sway length (COM) * | 1.29 ± 0.55 | 1.25 ± 0.39 |
| Mean sway velocity (COM) * | 1.29 ± 0.55 | 1.25 ± 0.39 |
| 95% CI circle area (COM) | 1.61 ± 1.43 | 1.50 ± 1.00 |
| 95% CI ellipse area (COM) | 1.39 ± 1.14 | 1.33 ± 0.80 |
| Mean sway area (COM) | 1.45 ± 1.08 | 1.40 ± 0.70 |

TABLE 2-continued

|  | | |
|---|---|---|
| Mean sway frequency (COM) | 1.25 ± 0.59 | 1.18 ± 0.49 |
| Mean ML sway frequency (COM) * | 1.19 ± 0.54 | 1.14 ± 0.54 |
| Mean AP sway frequency (COM) ^ | 1.29 ± 0.70 | 1.21 ± 0.49 |
| Inertial sensor | | |
| Mean RMS Acc | 1.00 ± 0.00 | 1.00 ± 0.00 |
| RMS Acc (ML) | 1.34 ± 0.64 | 1.16 ± 0.22 |
| RMS Acc (V) | 1.33 ± 0.63 | 1.17 ± 0.25 |
| RMS Acc (AP) | 1.62 ± 0.81 | 1.44 ± 0.37 |
| Mean RMS ang. vel. | 1.13 ± 0.51 | 1.01 ± 0.20 |
| RMS ang. vel. (ML) | 1.78 ± 1.22 | 1.49 ± 0.42 |
| RMS ang. vel. (V) | 1.99 ± 1.24 | 1.87 ± 0.66 |
| RMS ang. vel. (AP) | 1.40 ± 0.80 | 1.18 ± 0.24 |
| Median frequency Acc (Fmed) | 1.54 ± 0.92 | 1.28 ± 0.37 |
| Spectral edge frequency Acc (SEF) | 1.54 ± 0.52 | 1.49 ± 0.41 |
| Spectral entropy Acc (H) | 1.24 ± 0.20 | 1.22 ± 0.16 |

The results show some features having significantly different values between falters versus non-falters (e.g., with feature values having a $p<0.05$). For example, the mean sway frequency in either the ML or AP directions, calculated using the COM technique, both showed significant differences among falters and non-falters. A significant difference may be indicated by, for example, a $p<0.05$. In the same example, the RMS of the angular velocity along the ML, V, and AP axes while the participant's eyes were open showed significant differences between falters and non-fallers, as did the RMS of the acceleration. The same example further showed that features derived from center of pressure data calculated using the COM technique were more discriminating of falters versus non-fallers than features derived from center of pressure data calculated using the CHAT and CAAT techniques. A non-parametric hypothesis test (e.g. Mann-Whitney version of the Wilcoxon rank sum test) may be used to test for significant differences in feature values between falters versus non-falters.

In the example, various SVM classifier models were generated. The SVM models included a model based on features values calculated from all standing balance assessment trials; a model based on feature values calculated from trials involving only male participants; and a model based on feature values calculated from trials involving only female participants. The model that is based on feature values calculated from all trials yielded a mean classification accuracy of 76.25%. The model that is based on feature values calculated from trials involving only male participants yielded a mean classification accuracy of 87.80%. The model based on feature values calculated from trials involving only female participants yielded a mean classification accuracy of 84%. Other example values of the accuracy metrics, which were discussed above, are shown in Table 3. For comparison, an example SVM based on features calculated from data collected during a Berg Balance Scale (BBS) test yielded a mean classification accuracy of 62.92%.

TABLE 3

|  | All data | Male | Female |
|---|---|---|---|
| Acc (%) | 76.25 | 87.80 | 84.00 |
| Sens (%) | 73.38 | 78.71 | 81.47 |
| Spec (%) | 68.55 | 75.00 | 78.28 |
| PPV (%) | 73.38 | 78.96 | 81.47 |
| NPV (%) | 68.55 | 74.71 | 78.28 |

Figure 4:
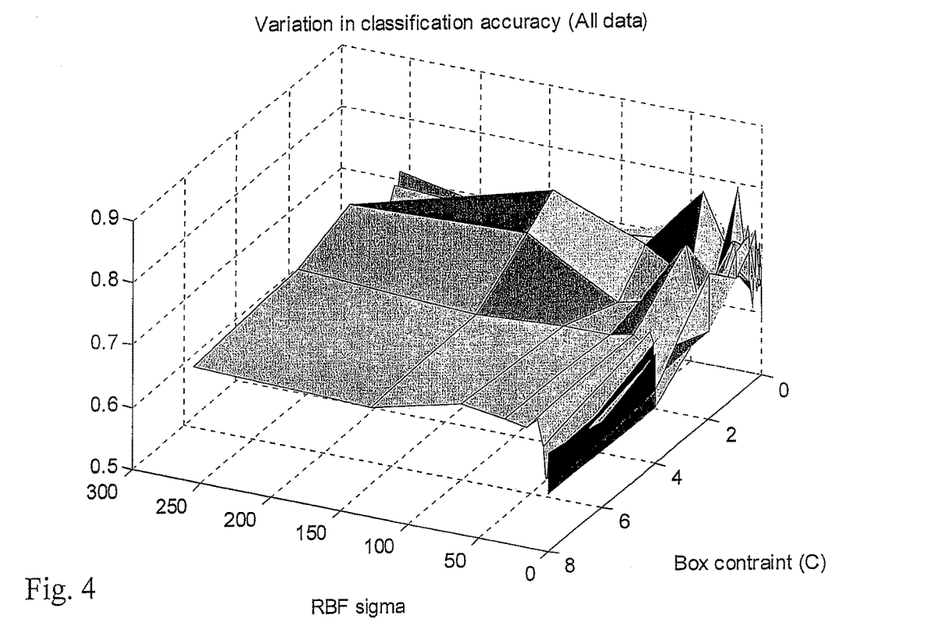
FIG. 4 illustrates example variations in classification accuracy with parameters for a falls risk classifier model that is based on data collected from both male and female balance assessment trial participants and under both eyes open conditions and eyes closed conditions.

FIGS. 4A-4C provide a graphical illustration of variation in classification accuracy of a SVM classifier model based on the selected value of the σ and box constraint C parameters of the classifier model. As illustrated in FIG. 4A, the SVM model generated from the trials of all participants yielded an optimal accuracy when σ=1 and C=2. As illustrated in FIG. 4B, the SVM model generated from the trials involving only male participants yielded an optimal classification accuracy when σ=2 and C=2. Further, as illustrated in FIG. 4C, the SVM model generated from the trials involving only female participants yielded an optimal classification accuracy when σ=1 and C=256.

The three separate models may be based on different sets of features. The features chosen for each model may have been determined from sequential forward feature selection. The selected features for the three example models are shown in Table 4.

TABLE 4

| All data<br>σ = 1, C = 2 | Male<br>σ = 2, C = 2 | Female<br>σ = 1, C = 256 |
|---|---|---|
| Sway length (COM) - EO | RMS dist (CAAT) - EO | Sway freq (COM) - EO |
| Sway freq (AP) (COM) - EO | 95% CI ellipse area (CAAT) - EO | Sway freq (AP) (COM) - EO |
| Sway length (COM) - EC | Sway freq (AP) (CAAT) - EO | RMS acc (AP) - EO |

TABLE 4-continued

| All data<br>$\sigma = 1, C = 2$ | Male<br>$\sigma = 2, C = 2$ | Female<br>$\sigma = 1, C = 256$ |
|---|---|---|
| 95% CI circle area (CAAT) - Romberg Ratio (R)<br>95% CI ellipse area (CAAT) - R | Sway freq (ML) (COM) - EC<br>95% CI circle area (CHAT) - R<br>Sway length (COM) - R<br>RMS ang. vel. (ML) - EO | SEF acc - EC<br>SEF acc - R |

In another example, a classifier model may be generated based solely on pressure sensor data or based solely on inertial sensor data. In another example, a classifier model may be generated based solely on sensor data from trials in which participants' eyes were closed, or solely on sensor data from trials in which participants' eyes were open. Example values for accuracy metrics for such various classifier models are shown in Table 5.

TABLE 5

|  | Pressure | Inertial | Pressure-EO | Inertial -EO | Pressure -EC | Inertial EC |
|---|---|---|---|---|---|---|
| Acc (%) | 76.25 | 76.12 | 75.39 | 70.86 | 62.16 | 69.33 |
| Sens (%) | 73.38 | 81.85 | 73.38 | 76.31 | 73.38 | 64.92 |
| Spec (%) | 68.55 | 63.82 | 71.27 | 59.27 | 55.27 | 74.55 |
| PPV (%) | 73.38 | 72.78 | 75.04 | 68.89 | 62.9 | 75.09 |
| NPV (%) | 68.55 | 74.84 | 69.14 | 67.92 | 56.61 | 64.26 |

Figure 5:
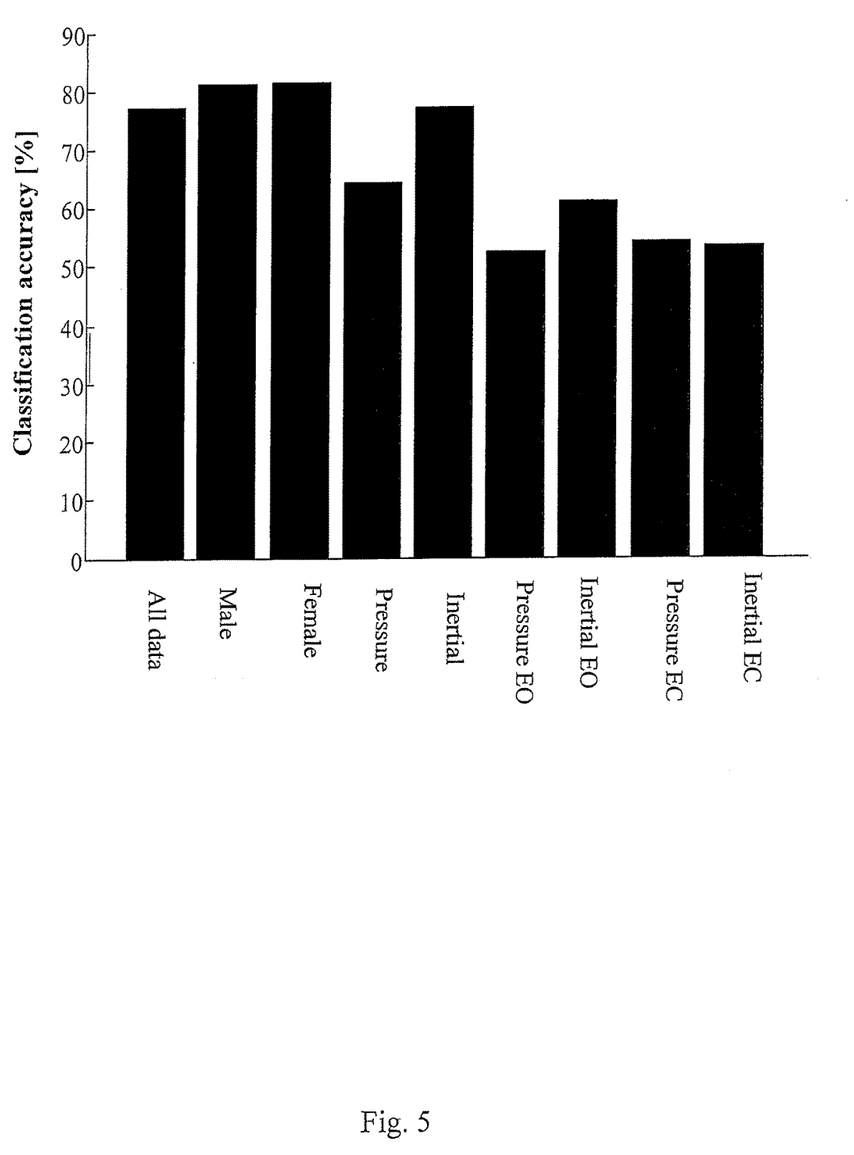
FIG. 5 illustrates example accuracy calculations of various falls risk classifier models derived from standing balance tasks.

An overall summary of classification accuracy values for various classifier models based on different subsets of features or feature values is shown in FIG. 5. Based on the example figure, a classifier model based on sensor data from both eyes open and eyes closed trials may yield greater accuracy than a classifier model based on only one of the types of trials. Having two separate classifier models that were each based on sensor data collected from only male participants or based on sensor data collected from only female participants may also yield greater accuracy than having a single classifier model based on sensor data collected from all participants. Further based on the example figure, having a classifier model that is based on both inertial sensor data and pressure sensor data may yield better accuracy than having a single model based on only pressure sensor data.

As discussed above, standing balance assessment trials (otherwise known as quiet standing) may be divided into those in which participants have their eyes open and those in which participants have their eyes closed.

Figure 6:
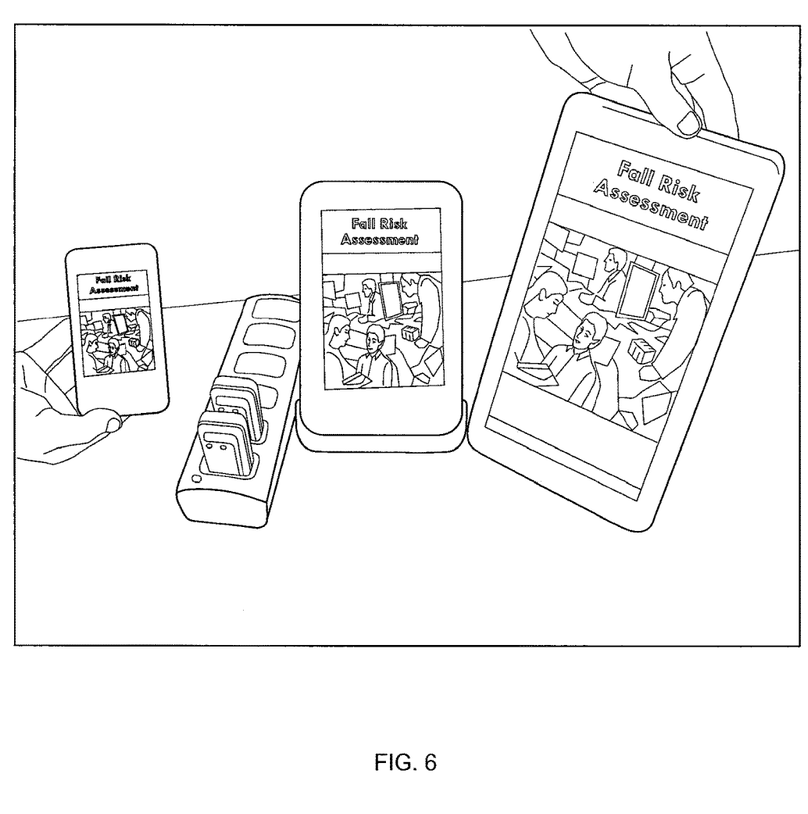
FIG. 6 illustrates a user interface for performing and displaying data relating to postural stability and falls risk assessment.

The falls risk estimation may be implemented on one or more processing devices. FIG. 6 illustrates various mobile computing devices that may each be configured to communicate (e.g., through a wireless connection) with inertial sensors and pressure sensors, to calculate feature values, or to generate falls risk estimates. The various computing devices may further be configured to output instructions to participants or other persons who are estimating their future risk of falling, and may be configured to output the estimated risk.

Those skilled in the art will appreciate from the foregoing description that the broad techniques of the embodiments of the present invention can be implemented in a variety of forms. Therefore, while the embodiments of this invention have been described in connection with particular examples thereof, the true scope of the embodiments of the invention should not be so limited since other modifications will become apparent to the skilled practitioner upon a study of the drawings, specification, and following claims.

What is claimed is:

1. A method for assessing falls risk using a system comprising at least one inertial sensor and at least one processor, the method comprising:
    performing a standing balance assessment of a person by:
    (a) receiving inertial sensor data using the at least one processor from the at least one inertial sensor configured to be attached to a lumbar region of the person; and
    (b) receiving pressure sensor data using the at least one processor from a pressure sensor matrix that is detecting pressure exerted by the person on the pressure sensor matrix, wherein the pressure sensor matrix comprises a plurality of pressure sensors; then
    generating center of pressure data for the person, using the at least one processor, based on at least the received pressure sensor data from the standing balance assessment;
    deriving a feature value indicative of when the person has fallen during a predetermined interval using the at least one processor;
    training a classifier model using the at least one processor to recognize the feature value, based on the received inertial sensor data and the center of pressure data, wherein the classifier model is configured to generate a prediction risk of future falls based on the center of pressure data and based on the inertial sensor data as input into the classifier model, and
    using the at least one processor to generate falls risk estimate based on the prediction risk of future falls to reduce the risk of future falls of the person.

2. The method of claim 1, wherein the classifier model is a support vector machine model.

3. The method of claim 2, wherein training the classifier model comprises relating values related to a statistical property of the inertial sensor data to the feature value indicative of when the person has fallen.

4. The method of claim 3, wherein the method further comprises determining using the at least one processor a root mean squared value of the inertial sensor data, wherein the inertial sensor data includes multi-axial acceleration data or multi-axial angular velocity data, and wherein the root mean squared value is used by the classifier model to determine the falls risk estimate indicative of falls risk.

5. The method of claim 3, wherein the method further comprises determining using the at least one processor a spectral edge frequency of the inertial sensor data, wherein the spectral edge frequency is determined based on a power spectrum of the inertial sensor data, the power spectrum being based on a frequency profile of a portion of the inertial sensor data, and wherein at least half of the power spectrum's power is at or below the spectral edge frequency.

6. The method of claim 3, wherein training the classifier model comprises determining a value of a pressure-based feature and relating the value of the pressure-based feature to the feature value indicative of when the person has fallen, wherein the pressure-based feature is related to a statistical property of the center of pressure data.

7. The method of claim 6, wherein the statistical property of the center of pressure data is indicative of how the person's center of pressure changes during an interval in which the pressure sensor data is received.

8. The method of claim 6, wherein training the classifier model comprises relating the feature value indicative of when the person has fallen with the person's age, gender, height, or weight.

9. The method of claim 1, wherein the method further comprises receiving inertial sensor data and pressure sensor data from a plurality of persons and training the classifier model to recognize feature patterns associated with falling using the at least one processor, and wherein the training of the classifier model is based on the inertial sensor data and the pressure sensor data from the plurality of persons, and wherein the plurality of persons includes only men or only women.

10. The method of claim 1, wherein the method further comprises receiving via the least one processor inertial sensor data and pressure sensor data from a plurality of persons, wherein the training of the classifier model is based on the inertial sensor data and the pressure sensor data from the plurality of persons, the plurality of persons all having eyes open or all having eyes closed during the receiving of the inertial sensor data and the pressure sensor data.

11. The method of claim 3, wherein the method further comprises determining using the at least one processor a root mean squared value of the inertial sensor data, wherein the inertial sensor data includes multi-axial acceleration data and multi-axial angular velocity data, and wherein the root mean squared values of multi-axial acceleration data and multi-axial angular velocity data are used by the classifier model to determine the falls risk estimate indicative of falls risk.

12. A system for assessing falls risk, comprising:
an inertial sensor configured to be attached to a lumbar region of a person;
a pressure sensor matrix, the pressure sensor matrix configured to sense a pressure exerted by the person thereon, wherein the pressure sensor matrix comprises a plurality of pressure sensors;
at least one processor configured to perform a standing balance assessment of a person by being configured to:
(a) receive inertial sensor data from the inertial sensor and (b) receive pressure sensor data from the pressure sensor matrix, wherein the at least one processor is further configured to:
generate center of pressure data for the person based on at least the received pressure sensor data from the standing balance assessment;
derive a feature value from the received inertial sensor data and/or the received pressure sensor data indicative of when the person has fallen during a predetermined interval,
train a classifier model using the at least one processor to recognize the feature value, based on the received inertial sensor data and the center of pressure data, wherein the classifier model is configured to generate a prediction risk of future falls based on the center of pressure data and based on the inertial sensor data input into the classifier model, and
use the at least one processor to generate falls risk estimate based on the prediction risk of future falls to reduce the risk of future falls of the person.

13. The system of claim 12, wherein the classifier model is a support vector machine model.

14. The system of claim 13, wherein the at least one processor is configured to relate values related to a statistical property of the inertial sensor data to the feature value indicative of when the person has fallen.

15. The system of claim 14, wherein the at least one processor is further configured to determine a root mean squared value of the inertial sensor data, wherein the inertial sensor data includes acceleration data or angular velocity data, and wherein the root mean squared value is used by the classifier model to determine the falls risk estimate indicative of falls risk.

16. The system of claim 14, wherein the at least one processor is further configured to determine a spectral edge frequency of the inertial sensor data, wherein the spectral edge frequency is determined based on a power spectrum of the inertial sensor data, the power spectrum being based on a power spectral density of a portion of the inertial sensor data, and wherein at least half of the signals' power is at or below the spectral edge frequency.

17. The system of claim 14, wherein the at least processor is configured to determine a value of a pressure-based feature and to relate the value of the pressure-based feature to the feature value indicative of when the person has fallen, wherein the pressure-based feature is related to a statistical property of the center of pressure data.

18. The system of claim 17, wherein the statistical property of the center of pressure data is indicative of how the person's center of pressure changes during an interval in which the pressure sensor data is received.

19. The system of claim 17, wherein the at least processor is configured to train the classifier model by relating the feature value indicative of falls risk of the person with the person's age, gender, height, or weight.

20. The system of claim 12, wherein the at least processor is further configured to receive inertial sensor data and pressure sensor data from a plurality of persons and training the classifier model to recognize feature patterns associated with falling, and wherein the training of the classifier model is based on the inertial sensor data and the pressure sensor data from the plurality of persons, and wherein the plurality of persons includes only men or only women.

21. A method for assessing falls risk using a system comprising at least one inertial sensor and at least one processor, comprising:
performing a standing balance assessment of a person by:
(a) receiving inertial sensor data by the at least one processor from the at least one inertial sensor configured to be attached to a lumbar region of the person; and
(b) receiving pressure sensor data using the at least one processor from a pressure sensor matrix that is detecting pressure exerted by the person on the pressure sensor matrix, wherein the pressure sensor matrix comprises a plurality of pressure sensors; then
generating center of pressure data for the person, using the at least one processor, based on at least the received pressure sensor data from the standing balance assessment; and
training a classifier model using the at least one processor to recognize a feature value indicative of when the person has fallen during a predetermined interval using the at least one processor, based on the received inertial sensor data and the center of pressure data, wherein the classifier model is configured to generate a prediction risk of future falls based on the center of pressure data and based on the inertial sensor data input into the classifier model, and using the at least one processor to generate falls risk estimate based on the prediction risk of future falls to reduce the risk of future falls of the person.

* * * * *